United States Patent [19]

Shirahata

[11] Patent Number: 5,136,074

[45] Date of Patent: Aug. 4, 1992

[54] SILYLATING AGENT

[75] Inventor: Akihiko Shirahata, Yotsukaidoo, Japan

[73] Assignee: Dow Corning Toray Silicone Company, LTD., Tokyo, Japan

[21] Appl. No.: 523,519

[22] Filed: May 15, 1990

[30] Foreign Application Priority Data

Jun. 8, 1989 [JP] Japan .................. 1-146242

[51] Int. Cl.$^5$ .............................................. C07F 7/08
[52] U.S. Cl. ................................... 556/489; 516/465
[58] Field of Search ......................... 556/465, 489

[56] References Cited

PUBLICATIONS

Bazant et al., "Organosilicon Compounds", vol. 2, part 1, Academic Press, N.Y. (1965), pp. 180, 181, 236–238.
J. Chem. Soc. (C), 1966; Organosilicon Compounds, Part XXXVII, Optical Resolution of p–(Ethylmethylphenylsilyl) benzoic Acid, by C. Eaborn and C. G. Pitt, pp. 1524–1527.

*Primary Examiner*—Paul F. Shaver
*Attorney, Agent, or Firm*—William F. Boley

[57] ABSTRACT

The present invention is a silylating agent of formula $$(CH_3)(R)(R^1)SiX;$$

where R is an isopropyl group, $R^1$ is a monovalent hydrocarbon group having 2 to 6 carbon atoms, and X is a chlorine atom or bromine atom. The silylating agent of the present invention provide silylation product which is much more stable than the silylation product obtained with trimethylchlorosilane, and its protective group is as stable as the silylation product obtained from t-butyldimethylchlorosilane. Moreover, the present described silylating agents are characterized by an easier desilylation than the t-butyldimethylsilyl group.

1 Claim, No Drawings

SILYLATING AGENT

BACKGROUND OF INVENTION

The present invention relates to a silylating agent suitable for the protection of active hydrogen during the execution of organic reactions.

Based on its commercial availability and cost, trimethylchlorosilane was a good earlier silylating agent for the protection of active hydrogen (for example, the hydroxyl group or amine NH) during the synthesis of pharmaceuticals, intermediates for chemical production, and so forth. However, silylation of the hydroxyl group or amine NH by the trimethylsilyl group did not always give satisfactory results because of this group's performance as a protective group during organic reactions, i. e., the chemical stability of the silylation product was inadequate. Due to this, t-butyldimethylchlorosilane became the leading silylating agent because it generates a protective group which is satisfactorily stable during the execution of organic reactions. Still, the t-butyldimethylsilyl group is in fact too stable, and fairly vigorous reaction conditions are required for the regeneration of active hydrogen in the desilylation reaction following execution of the necessary organic reaction(s). This also results in such problems as destruction of other functional groups.

The present invention seeks to solve the problems arising in the above-described prior art through the introduction of a silylating agent which will yield a very chemically stable silylation product, but which will also react more easily in the desilylation reaction than the t-butyldimethylsilyl group.

DESCRIPTION OF INVENTION

Accordingly, the present invention relates to a silylating agent as represented by the following general formula

$(CH_3)(R)(R^1)SiX;$ where R is the isopropyl group, $R^1$ is a monovalent hydrocarbon group having 2 to 6 carbon atoms, and X is the chlorine atom or bromine atom.

The silylating agent of the present invention provides a silylation product which is much more stable than the silylation product obtained from trimethylchlorosilane, and its protective group is as stable as the silylation product obtained from t-butyldimethylchlorosilane. Moreover, with regard to its behavior in the desilylation reaction, it is characterized by an easier desilylation than the t-butyldimethylsilyl group.

The group $R^1$ in the silylating agent used by the present invention is a monovalent hydrocarbon group which contains 2 through 6 carbon atoms. This comprises the phenyl group and monovalent aliphatic hydrocarbon groups having 2 to 6 carbons, and said monovalent aliphatic hydrocarbon groups comprise the $C_2$ through $C_6$ alkyl groups and their isomers. For groups having 3 or 4 carbon atoms, branched structures are preferred over linear structures. Preferred groups, for $R^1$, are the phenyl group and isopropyl group.

The silylating agent of the present invention is useful as a silylating agent during the production of pharmaceuticals, as intermediates for chemical synthesis, and so forth.

The silylation of amine NH or the hydroxyl group in carboxylic acids or alcohols using the silylating agent of the present invention affords a silylation product with a protective group which is much more stable than is the case for trimethylsilyl-based silylation products. In addition, there is little risk of destruction of other functional groups during hydrolytic desilylation since desilylation proceeds in the case of the invention at a velocity from 10 times to 100 times that for the tert-butyldimethylsilyl-based silylation product.

So that those skilled in the art may better understand and appreciate the instant invention, the following examples are presented. These examples are presented to be illustrative and are not to be construed as limiting the claims as delineated herein.

EXAMPLE 1

Synthesis of methylphenylisopropylchlorosilane. 36 g (1.5 mol) magnesium was introduced into a 2 L four-neck flask equipped with a reflux condenser, stirring rod, thermometer, and addition funnel, and was dried under nitrogen. 800 mL dry tetrahydrofuran (THF) was then added. A Grignard reagent was prepared by slowly dripping in 117.8 g (1.5 mol) isopropyl chloride from the addition funnel. Then, 267.7 g (1.4 mol) phenylmethyldichlorosilane was dripped in from the addition funnel. After completion of this addition, the reaction was brought to completion by continuing to stir for 5 hours at the reflux temperature of THF. After cooling to room temperature, 500 mL hexane was added, the reaction mixture was filtered, and the solvent was distilled from the filtrate. Continuing with distillation in vacuo afforded 258 g (1.3 mol) of the target methylphenylisopropylchlorosilane (bp=85 degrees Centigrade/7 mmHg).

EXAMPLE 2

Synthesis of methyldiisopropylchlorosilane. 73 g (3.0 mol) magnesium was introduced into a 2 L four-neck flask equipped with a reflux condenser, stirring rod, thermometer, and addition funnel, and was dried under nitrogen. 1,000 mL dry THF was then added. A Grignard reagent was prepared by slowly dripping in 235.6 g (3.0 mol) isopropyl chloride from the addition funnel. 166.8 g (1.45 mol) methyldichlorosilane was then dripped in from the addition funnel. After completion of this addition, the reaction was brought to completion by continuing to stir for 2 hours at the reflux temperature of THF, followed by the addition of 350 mL water, with cooling, for hydrolysis. The reaction solution was recovered by decantation, and the THF was distilled out through a 30 cm Widmer precision distillation column. Continuing with distillation at ambient pressure afforded 160 g (1.2 mol) methyldiisopropylsilane (bp=122 degrees Centigrade). 26.1 g (0.2 mol) of the methyldiisopropylsilane thus obtained was placed in a 50 mL three-neck flask equipped with a reflux condenser, thermometer, and addition funnel. 27 g (0.2 mol) sulfuryl chloride was carefully dripped in at 60 degrees Centigrade while stirring with a magnetic stirring bar. An exothermic reaction developed with the production of hydrogen chloride and sulfur dioxide. After addition of the entire quantity, the reaction was maintained for 1 hour at 70 degrees Centigrade and then distilled in vacuo. 27 g (0.16 mol) of the target methyldiisopropylchlorosilane (bp=64 degrees Centigrade32 mmHg) was obtained.

EXAMPLE 3

Synthesis of methyldiisopropylbromosilane. 20.8 g (0.16 mol) of the methyldiisopropylsilane prepared under Example 2, above, was placed in a 50 mL three-neck flask equipped with a reflux condenser, thermometer, and addition funnel. 25 g bromine (0.16 mol) was cautiously dripped in while cooling with ice and stirring with a magnetic stirring bar. A strong exothermic reaction developed, and hydrogen bromide was evolved. After addition of the entire quantity of bromine, the reaction was allowed to stand for 1 hour at room temperature and was then distilled in vacuo. 26.3 g (0.13 mol) of the target methyldiisopropylbromosilane (bp=92 degrees Centigrade/50 mmHg) was obtained.

EXAMPLE 4

Stability of silylation products against the alkoxy anion. This experiment concerned the synthesis of 4-siloxy-1-ethoxybutane by the action of sodium ethoxide on 4-siloxy-1-bromobutane in ethanol. The following results were obtained according to the substituent groups on the silicon atom: the reaction proceeded almost quantitatively for t-butyldimethyl and methyldiisopropyl; the reaction ran with a yield of 90% in the case of methylphenylisopropyl; and in the case of trimethyl, the target product was not obtained and trimethylethoxysilane was produced in large quantities.

EXAMPLE 5

Stability of silylation products against the Grignard reagent. A THF solution was prepared from equimolar quantities of cyclohexanol silylation product (Table 1) and cyclohexanone. To this was added a THF solution of an ethyl Grignard reagent in a quantity equivalent to the cyclohexanone. After hydrolysis, the yield of ethylcyclohexanol was measured. The results, as reported in Table 1, demonstrate that methyldiisopropylsiloxycyclohexane and methylphenylisopropylsiloxycyclohexane have an ethyl Grignard reagent stability equal to that of t-butyldimethylsiloxycyclohexane. In Table 1 and Table 2, Me=methyl, Ph=phenyl, t-Bu=tert-butyl, and iPr=isopropyl.

TABLE 1

| Stability of Silylation Products Against The Grignard Reagent. | |
|---|---|
| Silylation Product | Yield (%) of Ethylcyclohexanol |
| Me Ph i-Pr Si O $C_6H_{11}$ | 92 |
| Me i-$Pr_2$ Si O $C_6H_{11}$ | 95 |
| t-Bu $Me_2$ Si O $C_6H_{11}$ | 94 |
| $Me_3$ Si O $C_6H_{11}$ | 23 |

EXAMPLE 6

Desilylation reaction rate of the silylation products. The cyclohexanol silylation product (Table 2) was mixed at 3 weight% into ethanol containing 1 weight% concentrated hydrochloric acid, and the rate of cyclohexanol production was measured. This rate was first order in the concentration of cyclohexanol silylation product, and the first-order rate constants K are reported in Table 2. It is clear from these results that methyldiisopropylsiloxycyclohexane and methylphenylisopropylsiloxycyclohexane are more easily desilylated than t-butyldimethylsiloxycyclohexane.

TABLE 2

| Desilylation Reaction Rate of Silylation Products. | |
|---|---|
| Silylation Product | Cyclohexanol Production Rate Constant ($sec^{-1}$) |
| Me Ph i-Pr Si O $C_6H_{11}$ | $1.3 \times 10^{-2}$ |
| Me i-$Pr_2$ Si O $C_6H_{11}$ | $2.2 \times 10^{-1}$ |
| t-Bu $Me_2$ Si O $C_6H_{11}$ | $1.4 \times 10^{-3}$ |
| $Me_3$ Si O $C_6H_{11}$ | too fast to measure |

What is claimed is:

1. A silylating agent comprising a silane of formula $(CH_3)(R)(R^1)SiX$;

where R is an isopropyl group, $R^1$ is phenyl, and X is selected from a group consisting of chloride and bromide atoms.

* * * * *